United States Patent [19]

Mansy

[11] 4,303,543
[45] Dec. 1, 1981

[54] METHOD FOR CLEANSING AND CONDITIONING THE SKIN

[75] Inventor: Samir A. Mansy, Mason, Ohio

[73] Assignee: The Procter & Gamble Company, Cincinnati, Ohio

[21] Appl. No.: 59,708

[22] Filed: Jul. 23, 1979

Related U.S. Application Data

[63] Continuation of Ser. No. 15,838, Feb. 27, 1979, abandoned.

[51] Int. Cl.$^3$ .......................... C11D 9/30; C11D 9/48
[52] U.S. Cl. .................................... 252/117; 252/542; 252/545; 252/547; 252/DIG. 16
[58] Field of Search ............... 252/107, 117, 542, 547, 252/545, DIG. 15; 424/316, 329

[56] References Cited

U.S. PATENT DOCUMENTS

| | | | |
|---|---|---|---|
| 2,746,928 | 5/1956 | Darragh et al. | 252/106 |
| 2,861,955 | 11/1958 | Aylesworth | 252/117 |
| 2,950,255 | 8/1960 | Goff | 252/547 X |
| 3,186,912 | 6/1965 | Beamer | 424/59 |
| 3,408,298 | 10/1968 | Baravalle | 252/107 |
| 3,431,265 | 3/1969 | Wakeman et al. | 260/286 |
| 3,435,039 | 3/1969 | Wakeman et al. | 260/286 |
| 3,560,390 | 2/1971 | Gaines | 252/107 |
| 3,640,883 | 2/1972 | Gotte | 252/545 |
| 3,663,459 | 5/1972 | Yoshida et al. | 252/546 |
| 3,668,136 | 6/1972 | Barker | 252/117 |
| 3,687,870 | 8/1972 | Muzyczko et al. | 252/545 |
| 3,711,414 | 1/1973 | Hewitt | 252/118 |
| 3,838,057 | 9/1974 | Nicholas et al. | 252/117 |
| 3,954,846 | 5/1976 | Grignard | 260/501.15 |
| 4,001,394 | 1/1977 | Fogel et al. | 424/70 |
| 4,132,678 | 1/1979 | Iijima et al. | 252/545 |
| 4,235,759 | 11/1980 | Ohbu et al. | 252/545 |

FOREIGN PATENT DOCUMENTS

| | | |
|---|---|---|
| 868215 | 12/1978 | Belgium . |
| 525648 | 5/1956 | Canada . |
| 2416745 | 6/1975 | Fed. Rep. of Germany . |
| 442466 | 2/1936 | United Kingdom . |
| 641297 | 8/1950 | United Kingdom . |
| 757987 | 9/1956 | United Kingdom . |
| 759837 | 10/1956 | United Kingdom . |
| 1027898 | 4/1966 | United Kingdom . |
| 1050791 | 12/1966 | United Kingdom . |
| 1261231 | 1/1972 | United Kingdom . |
| 1370284 | 10/1974 | United Kingdom . |

OTHER PUBLICATIONS

Kitchener, J. A., "Surface Forces in the Deposition of Small Particles", J. Soc. Cosmet. Chem., 24, 709-725 (1973).

*Primary Examiner*—P. E. Willis, Jr.
*Attorney, Agent, or Firm*—Ronald L. Hemingway; Richard C. Witte

[57] ABSTRACT

Compositions for cleansing and conditioning the skin. The compositions comprise a soap and a conditioning agent which is a salt wherein the cation moiety is a protonated fatty amine or a fatty quaternary ammonium ion and the anion moiety is the anion of a fatty acid soap or an anionic synthetic detergent.

13 Claims, No Drawings

METHOD FOR CLEANSING AND CONDITIONING THE SKIN

REFERENCE TO RELATED APPLICATION

This is a continuation of application Ser. No. 015,838, filed Feb. 27, 1979, now abandoned.

TECHNICAL FIELD

The present invention relates to improvements in soap compositions for use on the skin. The improvements reside in the formulation of soap compositions which contain certain nitrogen-based conditioning agents. These conditioning agents are salts wherein the cation moiety is a protonated fatty amine or a fatty quaternary ammonium ion and the anion moiety is the anion of a fatty acid soap or an anionic synthetic detergent. The conditioning agents are present at levels of from about 0.25% to 25% by weight in the composition.

BACKGROUND ART

The most commonly used agent for cleansing the skin is soap. It has long been recognized that the cleansing of the skin with soap tends to remove natural oils from the skin, thereby causing skin dryness and roughness as well as a sensation of discomfort in the skin. Dryness and roughness can be perceived tactually by rubbing one's fingers across the skin and will be referred to herein as "external skin feel". Discomfort of the skin without touching (perceived as skin "tension" or "tightness") is felt internally by the person whose skin has been cleansed with soap and will be referred to herein as "internal skin feel". This internal feel is most readily perceived immediately after washing and drying of the skin.

There have been many attempts to alleviate the adverse skin effects caused by soap, by incorporating into soap compositions a variety of mildness additives. These have included vegetable oils, mineral oils, free fatty acids, fatty acid esters of polyols, and the like. While these materials tend to alleviate the negative effects of soap upon the skin, there is a continuing need for improved skin conditioners to be used with soap.

The object of the present invention is to provide soap compositions which are effective in cleansing the skin and are highly effective in alleviating the adverse effects on skin feel (especially external skin feel) which normally accompany the use of soap on the skin.

DISCLOSURE OF INVENTION

According to the present invention it has been found that certain salts wherein the cation moiety is a protonated fatty amine or a fatty quaternary ammonium ion, and the anion moiety is the anion of a fatty acid soap or an anionic synthetic detergent are effective in alleviating the adverse effects on external skin feel caused by washing the skin with soap.

The present invention encompasses skin cleansing compositions which comprise, a. from about 3% to about 95% by weight of a soap selected from the group consisting of alkali metal salts of fatty acids containing from about 8 to about 20 carbon atoms and mixtures of said soaps; and b. from about 0.25% to about 25% of a skin conditioning agent selected from compounds having the general formulas:

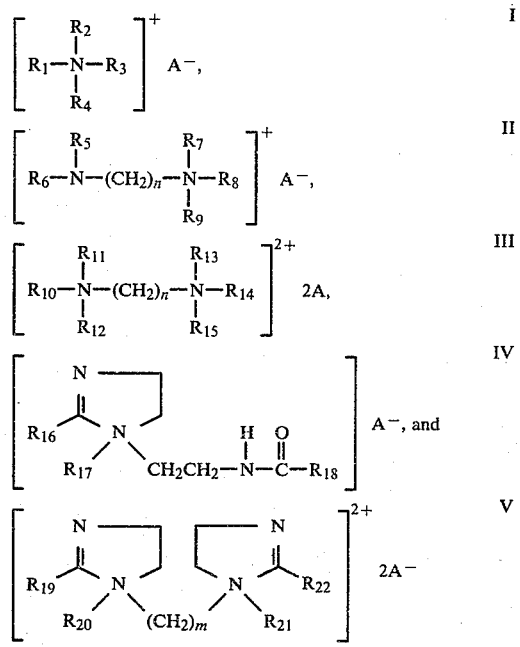

wherein $R_1$, $R_2$, $R_3$ and $R_4$ are each selected from the group consisting of hydrogen and aliphatic hydrocarbyl groups containing from 1 to about 24 carbon atoms, with at least one of $R_1$, $R_2$, $R_3$ and $R_4$ being an aliphatic hydrocarbyl group containing from about 8 to about 24 carbon atoms, wherein $R_5$, $R_6$, $R_7$, $R_8$ and $R_9$ are each selected from the group consisting of hydrogen and aliphatic hydrocarbyl groups containing from 1 to about 24 carbon atoms with at least one of $R_5$, $R_6$, $R_7$, $R_8$ and $R_9$ being an aliphatic hydrocarbyl group containing from about 8 to about 24 carbon atoms, wherein $R_{10}$, $R_{11}$, $R_{12}$, $R_{13}$ $R_{14}$ and $R_{15}$ are each selected from the group consisting of hydrogen and $C_1$ to $C_{24}$ aliphatic hydrocarbyl groups with at least one of $R_{10}$, $R_{11}$, $R_{12}$, $R_{13}$, $R_{14}$ and $R_{15}$ being an aliphatic hydrocarbyl group containing from about 8 to about 24 carbon atoms, wherein $R_{16}$, $R_{17}$ and $R_{18}$ are each selected from the group consisting of hydrogen and aliphatic hydrocarbyl groups containing from about 1 to about 24 carbon atoms, with at least one of $R_{16}$, $R_{17}$ and $R_{18}$ being an aliphatic hydrocarbyl group containing from about 8 to about 24 carbon atoms, wherein $R_{19}$, $R_{20}$, $R_{21}$ and $R_{22}$ are each selected from the group consisting of hydrogen and aliphatic hydrocarbyl groups containing from 1 to about 24 carbon atoms, with at least one of $R_{19}$, $R_{20}$, $R_{21}$ and $R_{22}$ being an aliphatic hydrocarbyl group containing from about 8 to about 24 carbon atoms, wherein n is an integer of from 1 to about 20, wherein m is an integer of from 2 to about 20 and wherein A is an anion which is selected from the group consisting of the anions of fatty acid soaps and anionic synthetic detergents. The term "hydrocarbyl" as used herein refers to a radical which consists of hydrogen and carbon atoms.

All percentages herein are "by weight" unless specified otherwise.

The Soap Component

The soap component of the present compositions is an alkali metal (e.g., sodium or potassium) soap or mixture of soaps of fatty acids containing from about 8 to about 24, preferably from about 10 to 20 carbon atoms.

The fatty acids used in making the soaps can be obtained from natural sources such as, for instance, plant or animal-derived glycerides (e.g., palm oil, coconut oil, babussu oil, soybean oil, castor oil, tallow, whale oil, fish oil, tallow, grease, lard and mixtures thereof). The fatty acids can also be synthetically prepared (e.g., by oxidation of petroleum stocks or by the Fischer-Tropsch process).

Alkali metal soaps can be made by direct saponofication of the fats and oils or by the neutralization of the free fatty acids which are prepared in a separate manufacturing process. Particularly useful are the sodium and potassium salts of the mixtures of fatty acids derived from coconut oil and tallow, i.e., sodium and potassium tallow and coconut soaps.

The term "tallow" is used herein in connection with fatty acid mixtures which typically have an approximate carbon chain length distribution of 2.5% $C_{14}$, 29% $C_{16}$, 23% $C_{18}$, 2% palmitoleic, 41.5% oleic and 3% linoleic (the first three fatty acids listed are saturated). Other mixtures with similar distribution, such as the fatty acids derived from various animal tallows and lard, are also included within the term tallow. The tallow can also be hardened (i.e., hydrogenated) to convert part or all of the unsaturated fatty acid moieties to saturated fatty acid moieties.

When the term "coconut oil" is used herein it refers to fatty acid mixtures which typically have an approximate carbon chain length distribution of about 8% $C_8$, 7% $C_{10}$, 48% $C_{12}$, 17% $C_{14}$, 9% $C_{16}$, 2% $C_{18}$, 7% oleic, and 2% linoleic (the first six fatty acids listed being saturated). Other sources having similar carbon chain length distribution such as palm kernel oil and babassu kernel oil are included with the term coconut oil.

When compositions of the present invention are prepared in the form of toilet bars the soap component is preferably either sodium soap or a mixture of sodium and potassium soap wherein the mixture contains no more than about 25% by weight potassium soap.

Also it is preferable in such bars that the total soap component comprises (a) from about 20% to 80% by weight of the soap component of a mixture containing soaps having from 8 to 14 carbon atoms and (b) from about 20% to 80% by weight of the soap component of soaps having from about 16 to 20 carbon atoms.

Soaps having such preferred chain length distribution characteristics can be realized by utilizing mixtures of tallow and coconut fatty acids in tallow/coconut weight ratios varying between 90:10 and 50:50.

The soap compositions herein can also contain free fatty acids having carbon chain lengths of from about 8 to 18. The presence of such free fatty acids tends to improve the speed and volume of lathering of the composition and confers a creamy feel to the lather. When free fatty acids are utilized in the compositions herein they are generally present at levels of from about 5% to about 25% of the total amount of soap.

Toilet bars containing the above-described soap mixtures, as well as their manufacture, are described in more detail in Megson et al, U.S. Pat. No. 3,576,749, issued Apr. 27, 1971, and White, U.S. Pat. No. 3,835,058, issued Sept. 10, 1974, Both of these patents are incorporated herein by reference.

The Skin Conditioning Component

The skin conditioning component of the present compositions is selected from the group of compounds having the formulas:

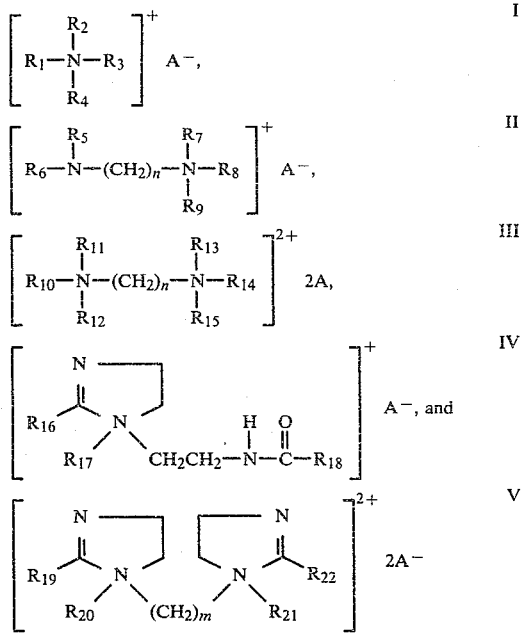

wherein $R_1$, $R_2$, $R_3$ and $R_4$ are each selected from the group consisting of hydrogen and aliphatic hydrocarbyl groups containing from 1 to about 24 carbon atoms, with at least one of $R_1$, $R_2$, $R_3$ and $R_4$ being an aliphatic hydrocarbyl group containing from about 8 to about 24 carbon atoms, wherein $R_5$, $R_6$, $R_7$, $R_8$ and $R_9$ are each selected from the group consisting of hydrogen and aliphatic hydrocarbyl groups containing from 1 to about 24 carbon atoms with at least one of $R_5$, $R_6$, $R_7$, $R_8$ and $R_9$ being an aliphatic hydrocarbyl group containing from about 8 to about 24 carbon atoms, wherein $R_{10}$, $R_{11}$, $R_{12}$, $R_{13}$ $R_{14}$ and $R_{15}$ are each selected from the group consisting of hydrogen and $C_1$ to $C_{24}$ aliphatic hydrocarbyl groups with at least one of $R_{10}$, $R_{11}$, $R_{12}$, $R_{13}$, $R_{14}$ and $R_{15}$ being an aliphatic hydrocarbyl group containing from about 8 to about 24 carbon atoms, wherein $R_{16}$, $R_{17}$ and $R_{18}$ are selected from the group consisting of hydrogen and aliphatic hydrocarbyl groups containing from 1 to about 24 carbon atoms, with at least one of $R_{16}$, $R_{17}$ and $R_{18}$ being an aliphatic hydrocarbyl group containing from about 8 to about 24 carbon atoms, wherein $R_{19}$, $R_{20}$, $R_{21}$ and $R_{22}$ are selected from the group consisting of hydrogen and aliphatic hydrocarbyl groups containing from 1 to about 24 carbon atoms, with at least one of $R_{19}$, $R_{20}$, $R_{21}$ and $R_{22}$ being an aliphatic hydrocarbyl group containing from about 8 to about 24 carbon atoms, wherein n is an integer of from 1 to about 20 (preferably from 1 to about 4), wherein m is an integer of from 2 to about 20 (preferably 2 to 4) and wherein A is an anion which is selected from the group consisting of the anions of fatty acid soaps and anionic synthetic detergents.

These skin conditioning compounds are salts. The cation moiety of the salt is a protonated fatty amine or protonated imidazoline moiety or a quaternary ammonium or imidazolinium moiety. For example, in Formula I, when one or more of the "R" groups is hydrogen, the cation is a protonated amine moiety. If all four "R" groups are hydrocarbyl groups, the cation is a quaternary ammonium moiety.

Amines can be protonated by reacting them with an acidic material (e.g., HCl or acetic acid). The resulting compound is a protonated amine salt, e.g., an amine hydrochloride or an amine acetate. Amines which are protonated to provide cation moieties for the present invention can be primary, secondary or tertiary amines, and must contain at least one aliphatic hydrocarbyl group of from 8 to 24 carbon atoms. Examples of such amines are dodecylamine, methyl octadecyl amine, dimethyl hexadecyl amine, didodecyl methyl amine, ethyl dodecyl octadecyl amine, N-tetradecyl, N'propyl-1,3-propane diamine, 1-stearylamidoethyl-2-stearyl imidazoline and 1-ethylene bis(2-stearyl imidazoline). Examples of protonated amine salts formed from these amines are dodecylamine acetate, methyl octadecyl amine hydrochloride, dimethyl hexadecylamine hydrochloride, didodecyl methyl amine acetate ethyl dodecyl octadecyl amine acetate, N-tetradecyl, N'-propyl-1,3-propane diamine dihydrochloride, 1-stearylamidoethyl-2-stearyl imidazolinium hydrochloride and 1-ethylene bis(2-stearylimidazolinium)dihydrochloride. Such amine salts can be used to provide the protonated amine moiety which can serve as the cation of the skin conditioning agents of the present invention.

The quaternary ammonium ions are the cations which are formed by quaternizing a tertiary aliphatic amine with an additional aliphatic group. This is accomplished by reacting a tertiary amine with an alkylating agent such as methyl chloride. For example, if didodecyl methyl amine is reacted with methyl chloride the resulting quaternary ammonium salt is didodecyldimethylammonium chloride. Examples of specific quaternary ammonium salts which can be used to provide the quaternary ammonium cation moiety for the skin conditioning agents herein are didodecyldimethylammonium chloride, dodecyltrimethylammonium bromide, dihexadecyldimethylammonium acetate, N,N'-ditetradecyl-N,N,N',N'-tetramethyl-1,3-propyl diammonium dichloride, N,N'-distearyl-N,N,N',N'-tetramethyl-1,10-decyl diammonium diacetate, 1-methyl-1-stearylamidoethyl-2-stearyl imidazolinium methylsulfate and 1-ethylene bis(2-stearyl, 1-methylimidazolinium)dichloride.

The conditioning agents of the present invention are prepared by simple reaction between a protonated amine or imidazoline salt (e.g., hydrochloride) or a quaternary ammonium or imidazolinium salt, and a fatty acid soap or an anionic synthetic detergent. For example:

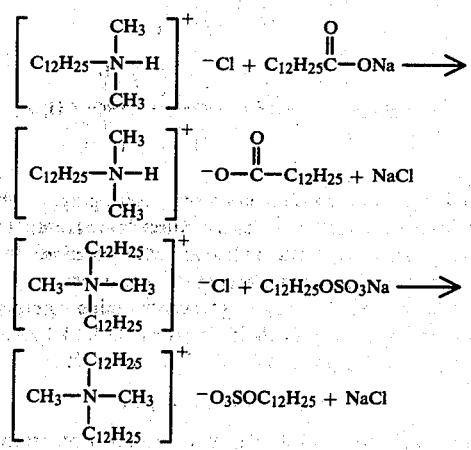

In the case where the cationic moiety is a protonated amine or imidazoline, the conditioning agent can also be prepared by reacting the free amine or imidazoline with a fatty acid (instead of a soap) or the acid form of the synthetic detergent (instead of the salt form of the detergent). For example:

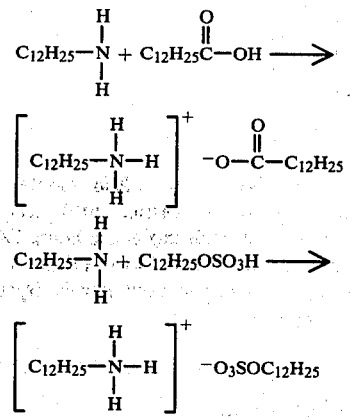

The anion moiety of the skin conditioning agent herein can be the anion of a fatty acid soap (i.e., the radical $$R_{23}-\overset{O}{\underset{\|}{C}}O^-$$

wherein $R_{23}$ is a $C_7$ to $C_{23}$ aliphatic group) or the anion of an anionic synthetic detergent. Any anionic synthetic detergent can be used to provide the anion moiety for the skin conditioning agents herein. The most common types of anionic synthetic detergents are the water soluble salts (e.g., sodium, potassium, lithium or ammonium) of organic sulfuric reaction products having in their molecule an aliphatic group containing from about 8 to about 24 carbon atoms, and a sulfonic or sulfuric acid ester radical. Synthetic detergents containing a $C_8$ to $C_{24}$ aliphatic group and having a carboxylic acid radical instead of a sulfonic or sulfuric acid ester radical can also be used. Examples of anionic synthetic detergents which can provide the anion moiety of the skin conditioning agents herein include the following:

1. Alkyl sulfates of the formula $R_{24}OSO_3M$ wherein $R_{24}$ is an alkyl (straight or branched chain) of from 8 to about 24 carbon atoms and M is an alkali metal or ammonium ion. Specific examples are sodium dodecyl sulfate and potassium hexadecyl sulfate.

2. Alkyl sulfonates of the formula $R_{24}SO_3M$ wherein $R_{24}$ and M are as defined in (1) above. These surfactants are also called paraffin sulfonates. Specific examples are sodium dodecyl sulfonate and ammonium octadecyl sulfonate.

3. Alkyl ether sulfates of the formula $R_{24}(OC_2H_4)_xOSO_3M$ wherein $R_{24}$ and M are as defined in (1) above and wherein x is a number of from 1 to 10. Specific examples are $C_{14}H_{29}(OC_2H_4)_3OSO_3Na$ and $C_{18}H_{37}(OC_2H_4)_5K$.

4. Alkyl monoglyceride sulfonates of the formula

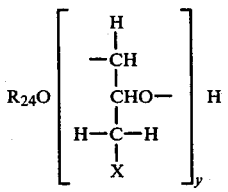

wherein y is a number of from 1 to 4, X is selected from the group consisting of chlorine, hydroxyl and —SO$_3$M, at least one X in each molecule being SO$_3$M, and wherein $R_{24}$ and M are defined as in (1) above (see U.S. Pat. No. 3,024,273 incorporated herein by reference). A specific example is $$C_{16}H_{33}OCH_2\underset{OH}{\overset{|}{C}}HCH_2SO_3Na.$$

5. Alkyl benzene sulfonates of the formula

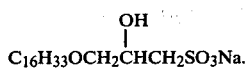

wherein $R_{24}$ and M are as defined in (1) above. Specific examples are dodecylbenzene sodium sulfonate and tridecylbenzene potassium sulfonate.

6. Acyl lactylates of the formula

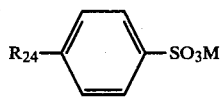

wherein $R_{24}$ and M are as defined in (1) above, and z is usually a number of from 1 to 3. A specific example is sodium stearoyl-2-lactylate.

Following is a listing of representative examples of skin conditioning agents of the present invention:

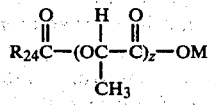

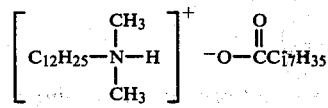

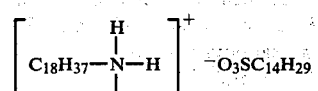

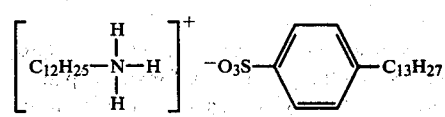

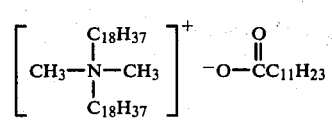

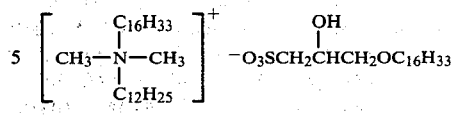

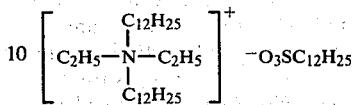

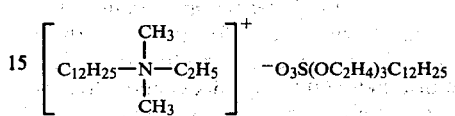

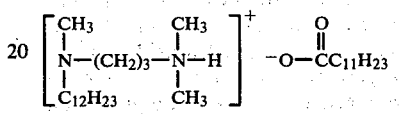

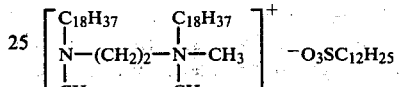

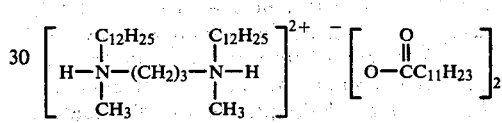

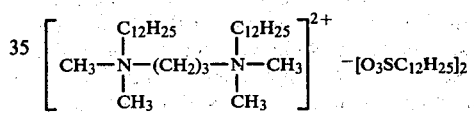

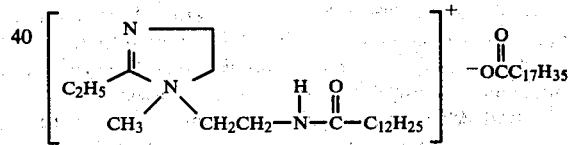

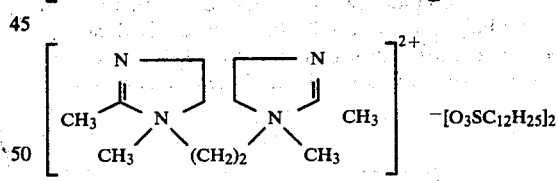

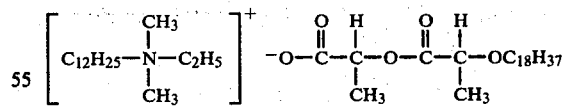

Examples of preferred skin conditioning agents of the present invention are stearylammonium laurate, stearylammonium stearate, distearyldimethylammonium laurate, and distearyldimethylammonium stearate.

Generally the ratio of soap to conditioning agent in the compositions herein will be from about 1:1 to about 100:1, preferably from about 3:1 to about 20:1.

Optional Components

The soap compositions of the present invention will normally contain water. When the compositions are in the form of a lotion or cream the water content will be of the order of 50% to about 95%. When the compositions are formulated into toilet bars, the water content will normally be of the order of 20% or less.

Conventional antibacterial agents can be included in the present composition at levels of from about 0.5% to about 4%. Typical antibacterial agents which are suitable for use herein are 3,4-di- and 3,4',5-tribromosalicyla-anildes; 4,4'-dichloro-3-(trifluoromethyl)carbanilide; 3,4,4'-trichlorocarbanilide and mixtures of these materials.

Conventional nonionic emollients can be included as additional skin conditioning agents in compositions of the present invention at levels up to about 40%, preferably at levels of from about 1% to about 25%. Such materials include, for example, mineral oils, paraffin wax having a melting point of from about 100° F. to about 170° F., fatty sorbitan esters (see U.S. Pat. No. 3,988,255, Seiden, issued Oct. 26, 1976, incorporated by reference herein), lanolin and lanolin derivatives, esters such as isopropyl myristate and triglycerides such as coconut oil or hydrogenated tallow. These nonionic-type skin conditioning agents appear to primarily contribute internal skin feel advantages to the compositions herein, whereas the aforedescribed protonated amine or quaternary salt conditioning agents appear to primarily contribute external skin feel advantages.

Free fatty acid such as coconut oil fatty acid can be added to the compositions herein to improve the volume and quality (creaminess) of the lather produced by the compositions herein.

Conventional perfumes, dyes and pigments can also be incorporated into compositions of the invention at levels up to about 5%. Perfumes are preferably used at levels of from about 0.5% to 3% and dyes and pigments are preferably used at levels of from about 0.001% to about 0.5%.

Polymeric materials such as polyacrylamide, which provide a slippery feel and enhance the deposition of the skin conditioning agents onto the skin can also be incorporated at levels of up to 2.5%, preferably from about 0.3% to about 1%. The addition of polyacrylamide to the compositions of my invention was not invented by me and I do not specifically claim it as part of my invention. It is described in more detail in the copending application of Wong and Jacobs, entitled CLEANSING AND CONDITIONING COMPOSITIONS FOR THE SKIN, Ser. No. 059,711, filed July 23, 1979, incorporated by reference herein.

Synthetic detergents can also be present in compositions herein. Preferred types of synthetic detergents are of the anionic or nonionic type. Examples of anionic synthetic detergents are the salts of organic sulfuric reaction products described in (1) through (5) hereinbefore. Examples of nonionic synthetic detergents are ethoxylated fatty alcohols (e.g., the reaction product of one mole of coconut fatty alcohol with from about 3 to 30 moles of ethylene oxide, the reaction product of one mole of coconut fatty acid with from about 3 to 30 moles of ethylene oxide and fatty acid amides such as coconut fatty acid monoethanolamide and stearic acid diethanolamide. Although it may be desirable in some instances to incorporate synthetic detergents into the compositions of the present invention, the compositions herein can be free of synthetic detergents. Synthetic detergents when present are normally employed at levels of from about 5% to about 400% by weight of the amount of soap in the compositions.

Insoluble alkaline earth metal soaps such as calcium stearate and magnesium stearate can also be incorporated into compositions of the present invention at levels up to about 30%. These materials are particularly useful in toilet bars in which synthetic detergents are present in that they tend to reduce the relatively high solubility which such bars normally have. These alkaline earth metal soaps are not included within the term "soap" as otherwise used in this specification. The term "soap" as used herein refers to the alkali metal soaps.

Lotions or creams can optionally contain thickeners or phase stabilizers such as carboxymethyl cellulose or xanthan gum.

Composition Preparation

The compositions of the present invention can be prepared in the form of toilet bars, or if desired, in the form of creams or lotions. The toilet bar is the most preferred form since this is the form of cleansing agent most commonly used to wash the skin.

Preferably the toilet bars are made from a mixture of soaps derived from coconut oil and hydrogenated tallow, the ratio of coconut soap to tallow soap being from about 1:1 to about 1:4. The toilet soap compositions generally contain from about 5% to about 20% moisture.

Toilet bars of the present invention can be prepared in the conventional manner. Moisture-containing base soap can be admixed with the conditioning agent and other optional ingredients such as perfumes, dyes, etc. in an amalgamator, milled in the conventional manner under conventional conditions, and extruded into logs for cutting and stamping into toilet bars. Alternatively, the skin conditioning agent can be co-melted with the base soap and then cooled to solidify the mixture before introduction into the amalgamator.

In making lotions or creams, the conditioning agent is thoroughly mixed with an aqueous solution or dispersion of the soap.

Toilet bars of the invention generally comprise from about 10% to about 90% (preferably from 60% to 90%) soap and from about 1% to about 25% (preferably from about 5% to about 15%) of the conditioning agents of the invention. Creams generally comprise from about 10% to about 45% soap and from about 0.5% to about 15% conditioning agent. Lotions generally comprise from about 3% to about 15% soap and from about 0.25% to about 5% conditioning agent. Creams generally contain from about 50% to about 75% water, and lotions about 75% to about 95% water.

The compositions of the invention can be used to prepare articles for cleansing the skin. These articles can comprise an absorbent paper or woven or nonwoven cloth which is impregnated with a composition of the invention. For example, a nonwoven cloth can be impregnated with an aqueous solution of a toilet bar composition of the invention and then subjected to a drying process which drives off sufficient water to reduce the moisture content to about 20% or less of the composition, thereby producing a cleansing article which is dry to the touch. Generally the amount of composition on the substrate should be sufficient to produce a composition:substrate ratio of about 0.5:1 to 5:1. When it is used it is simply wetted with water and used in the usual manner of a wash cloth.

Composition Use

The compositions of the present invention are used in the conventional manner of skin cleansing agents, i.e., they are applied to the skin and then the skin is rinsed with water. In the case of lotions and creams the composition can be totally applied "as is" to the skin. In the case of toilet bars, a solution or dispersion of the composition is formed prior to application by wetting the surface of the bar or rubbing the bar onto a wet washcloth. The wet bar or the wet washcloth which contains a portion of the composition is then rubbed against the skin.

Accordingly, the present invention also includes a method for cleansing and conditioning the skin, said method comprising the steps of (1) applying to the skin a composition of the invention and (2) rinsing the skin with water.

The invention will be further illustrated by the following examples:

EXAMPLE I

A toilet bar of the following composition was prepared.

| | |
|---|---|
| Soap (50/50 Tallow/Coconut) | 54.9% |
| Coconut Fatty Acid | 4.5 |
| Paraffin Wax (M.P. 133° F.)* | 24.8 |
| Stearylammonium Laurate | 5.0 |
| Polyacrylamide** | 0.5 |
| Dye | 0.001 |
| TiO$_2$ | 0.3 |
| Perfume | 1.0 |
| NaCl | 0.8 |
| EDTA | 0.06 |
| Moisture | 8.14 |

*Factowax R-133 - Standard Oil Co. of Ohio
**Serapan AP 273P - Dow Chemical Co.

12.94 lbs. of 50/50 tallow/coconut soap noddles (about 85.5% soap, 7% coconut fatty acid, 7% moisture and 0.5% NaCl) were mixed in an amalgamator with 5 lbs. paraffin wax, 1 lb. of stearylammonium laurate, 0.1 lbs. of polyacrylamide, 17 grams of a 1% aqueous dye solution, 0.06 lbs. of TiO$_2$, 0.2 lbs. of perfume and 0.454 lbs. of an aqueous solution of 22.3% NaCl and 2.7% sodium ethylenediamine tetraacetate. The paraffin had been premilled by one pass through a 3-roll soap mill and the stearylammonium laurate had been preflaked by placing a melt on chill rolls.

This mixture of ingredients was then passed through the 3-roll soap mill 2 times at a temperature of 98° F. The resulting flakes were then stored in an airtight container at 100° F. overnight. The next day the flakes were milled a final time at 98° F., plodded under vacuum and stamped into bar form.

A panel of 27 women lathered the above bar soap composition (test product) on to a prewashed terry cloth and each woman washed one half of her face as she normally would. The product was then spray rinsed off the skin by a 10 second spray of 90°–95° F. water. The skin was pat dried with a paper towel. The second half of the face was then washed in the same manner with a bar of a control product which was the same as the above soap composition except that it did not contain the paraffin wax, stearylammonium laurate and polyacrylamide.

The women were then asked which produce they preferred for internal skin feel and external skin feel immediately after drying the skin, and for external skin feel 15 minutes later. Results were as follows:

| | Internal Skin Feel | | External Skin Feel | |
|---|---|---|---|---|
| | Test Product | Control Product | Test Product | Control Product |
| Immediately after drying | 18 | 9 | 18 | 9 |
| 15 Minutes later | — | — | 18 | 5 |

EXAMPLE II

A lotion of the present invention is prepared as follows.

1 lb. of the toilet bar composition prepared according to Example I (prior to being plodded and stamped into bars), along with 0.008 lbs. of xanthan gum, are homogeneously dispersed into 3 lbs. of water by high shear mixing. The resulting skin cleansing lotion has the following formula:

| | |
|---|---|
| Soap (50/50 Tallow/ Coconut) | 13.7% |
| Coconut Fatty Acid | 1.1 |
| Paraffin Wax (M.P. 133° F.) | 6.2 |
| Stearylammonium Laurate | 1.25 |
| Polyacrylamide | 0.13 |
| Dye | 0.00025 |
| TiO$_2$ | 0.075 |
| Perfume | 0.25 |
| NaCl | 0.2 |
| EDTA | 0.015 |
| Xanthan Gum | 0.2 |
| Water | 76.9 |

EXAMPLE III

This example illustrates an alternate method of preparing a toilet bar of the present invention. 11.9 lbs. of 50/50 tallow/coconut sodium soap noodles (81.5%–82.5% soap, 7% coconut fatty acid, 10–11% moisture and 0.5% NaCl) are added to an amalgamator. 0.4 lbs. of water, 0.2 lbs. of perfume, 0.6 lbs. of TiO$_2$ and 0.07 lbs. of a 1% aqueous dye solution are then added and mixing is continued until the batch reaches a homogenous color (about 5 minutes). 0.10 lbs. of polyacrylamide (Separan AP 273P from Dow Chemical Company) is then added and mixing is continued for an additional 5 minutes. The mixture is then transferred to a 3-roll soap mill (operating at about 95° F., milled twice and stored overnight in an airtight container at 100° F.

The following day the stored soap flakes are added to an amalgamator. A co-melt of 5 lbs. of paraffin wax (Mobilwax 130 from Mobil Oil Company) and 2 lbs. of stearylammonium laurate which has been obtained by heating to about 180° F. is poured over the soap flakes while they are being mixed in the amalgamator. Mixing is continued until the temperature of the mixture drops to about 110° F. The contents are then removed from the amalgamator and milled twice into flakes, using the 3-roll soap mill operating at 95° F. to 100° F. The milled flakes are held overnight at 100° F. and milled a final time on the 3-roll mill. The milled flakes are then plodded under vacuum (barrel temperature about 95° F., nozzle temperature about 110° F.) and stamped into bars.

What is claimed is:

1. A method of cleansing and conditioning the skin comprising the steps of:
   1. Applying to the skin a composition comprising;
      a. from about 3% to about 95% by weight of a soap selected from the group consisting of alkali metal salts of fatty acids containing from about 8 to about 20 carbon atoms and mixtures of said soaps; and
      b. from about 0.25% to about 25% of a skin conditioning agent selected from;
         I. Stearylammonium laurate, stearylammonium stearate, distearyldimethylammonium laurate and distearyldimethylammonium stearate,

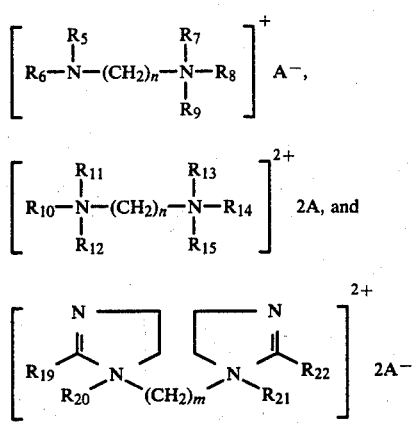

wherein $R_5$, $R_6$, $R_7$, $R_8$ and $R_9$ are each selected from the group consisting of hydrogen and aliphatic hydrocarbyl groups containing from 1 to about 24 carbon atoms with at least one of $R_5$, $R_6$, $R_7$, $R_8$ and $R_9$ being an aliphatic hydrocarbyl group containing from about 8 to about 24 carbon atoms, wherein $R_{10}$, $R_{11}$, $R_{12}$, $R_{13}$ $R_{14}$ and $R_{15}$ are each selected from the group consisting of hydrogen and $C_1$ to $C_{24}$ aliphatic hydrocarbyl groups with at least one of $R_{10}$, $R_{11}$, $R_{12}$, $R_{13}$, $R_{14}$ and $R_{15}$ being an aliphatic hydrocarbyl group containing from about 8 to about 24 carbon atoms, wherein $R_{19}$, $R_{20}$, $R_{21}$ and $R_{22}$ are each selected from the group consisting of hydrogen and aliphatic hydrocarbyl groups containing from 1 to about 24 carbon atoms, with at least one of $R_{19}$, $R_{20}$, $R_{21}$ and $R_{22}$ being an aliphatic hydrocarbyl group containing from about 8 to about 24 carbon atoms, wherein n is an integer of from 1 to about 20, wherein m is an integer of from 2 to about 20 and wherein A is an anion which is selected from the group consisting of the anions of fatty acid soaps and anionic synthetic detergents; wherein the weight ratio of soap to conditioning agent is from about 3:1 to 100:1 and wherein said composition is substantially free of synthetic detergents; and
   2. Rinsing the skin with water.

2. The method of claim 1 wherein the ratio of soap to skin conditioning agent is from about 3:1 to about 20:1.

3. The method of claim 2 wherein "n" in formulas II and III is an integer of from 1 to about 4 and wherein "m" in formula IV is an integer of from 2 to about 4.

4. The method of claim 3 wherein the composition is in the form of a toilet bar which comprises from about 10% to about 90% soap and from about 5% to about 15% conditioning agent.

5. The method of claim 4 wherein the composition comprises from about 60% to about 90% soap and from about 5% to about 15% conditioning agent.

6. The method of claim 5 wherein the soap is a mixture of soaps wherein said mixture comprises from about 20% to about 80% of soaps containing from 8 to 14 carbon atoms and from about 80% to about 20% of soaps containing from 16 to 20 carbon atoms.

7. The method of claim 6 wherein the conditioning agent is selected from the group consisting of stearylammonium laurate, stearylammonium stearate, distearyldimethylammonium laurate and distearyldimethylammonium stearate.

8. The method of claim 3 wherein the composition is in the form of a lotion, comprising from about 3% to about 15% soap, from about 0.25% to about 5% skin conditioning agent and from about 75% to about 95% water.

9. The method of claim 8 wherein the soap is a mixture of soaps wherein said mixture comprises from about 20% to about 80% of soaps containing from 8 to 14 carbon atoms and from about 80% to about 20% of soaps containing from 16 to 20 carbon atoms.

10. The method of claim 9 wherein the skin conditioning agent is selected from the group consisting of stearylammonium laurate, stearylammonium stearate, distearyldimethylammonium laurate and distearyldimethylammonium stearate.

11. The method of claim 3 wherein the composition is in the form of a cream comprising from about 10% to about 45% soap, from about 0.5% to about 15% skin conditioning agent and from about 50% to about 75% water.

12. The method of claim 11 wherein the soap is a mixture of soaps wherein said mixture comprises from about 20% to about 80% of soaps containing from 8 to 14 carbon atoms and from about 80% to about 20% of soaps containing from 16 to 20 carbon atoms.

13. The method of claim 12 wherein the skin conditioning agent is selected from the group consisting of stearylammonium laurate, stearylammonium stearate, distearyldimethylammonium laurate and distearyldimethylammonium stearate.

* * * * *